United States Patent
Wedekamp

(12) 
(10) Patent No.: US 6,231,820 B1
(45) Date of Patent: May 15, 2001

(54) UV DISINFECTING DEVICE ADVANTAGEOUS FOR FLUIDS FLOWS

(76) Inventor: Horst Wedekamp, Elverdisser Str. 92, D-32052 Herford (DE)

( * ) Notice: Subject to any disclaimer, the term of this patent is extended or adjusted under 35 U.S.C. 154(b) by 0 days.

(21) Appl. No.: 09/331,382

(22) PCT Filed: Dec. 19, 1997

(86) PCT No.: PCT/EP97/07174

§ 371 Date: Jul. 8, 1999

§ 102(e) Date: Jul. 8, 1999

(87) PCT Pub. No.: WO98/27011

PCT Pub. Date: Jun. 25, 1998

(30) Foreign Application Priority Data

Dec. 19, 1996 (DE) .............................................. 196 53 083

(51) Int. Cl.⁷ .................................................. B01J 19/12
(52) U.S. Cl. ...................................... 422/186.3; 210/748
(58) Field of Search ........................ 422/186.3; 210/748; 250/435

(56) References Cited

U.S. PATENT DOCUMENTS

| | | | |
|---|---|---|---|
| 3,061,721 | * 10/1962 | Brenner | 250/43 |
| 4,367,410 | 1/1983 | Wood | 250/437 |
| 4,482,809 | 11/1984 | Maarschalkerweerd | 250/436 |
| 4,767,932 | 8/1988 | Ellner | 250/435 |
| 4,825,083 | 4/1989 | Latel et al. | 250/436 |
| 5,124,131 | 6/1992 | Wekhof | 422/186.3 |
| 5,539,210 | * 7/1996 | Maarschalkerweerd | 250/372 |
| 5,660,719 | * 8/1997 | Kurtz et al. | 210/748 |
| 5,792,433 | * 8/1998 | Kadoya | 422/186.3 |
| 5,846,437 | * 12/1998 | Whitby et al. | 210/748 |
| 5,937,266 | * 8/1999 | Kadoya | 422/186.3 |

FOREIGN PATENT DOCUMENTS 2 030 694    4/1980   (GB) .

* cited by examiner

Primary Examiner—Kathryn Gorgus
Assistant Examiner—Theo Tran
(74) Attorney, Agent, or Firm—Woodbridge & Associates, P.C.; Richard C. Woodbridge

(57) ABSTRACT

A UV disinfecting device for flowing fluids, having a frame (1) and a certain number of lamp units (3) with UV lamps, whereby the lamp units each have at least one electrical connection and are held by the frame (1) substantially parallel and spaced from each other. For securing the lamp units (3), clamps (10, 14) are provided, which are particularly favorable for fluid flow. Preferably, each lamp is encased in a respective casing tube (6) having one or more elastomeric end stoppers (7) and the clamps are metallic leaf springs which engage the stoppers. The electrical leads pass through the stoppers. This facilitates easy replacement of failing lamps.

19 Claims, 3 Drawing Sheets

UV DISINFECTING DEVICE ADVANTAGEOUS FOR FLUIDS FLOWS

FIELD OF THE INVENTION

The present invention relates to a UV disinfecting device for flowing fluids, with a plurality of UV-emitting lamps arranged in parallel.

BACKGROUND

Such devices are installed in the clarified effluent flow from a sewage treatment plant. This effluent flow is conveyed through an open canal into which the UV disinfecting devices of this type are inserted. Elongated UV emitters, in the form of gas-discharge lamps, are disposed essentially horizontally and with their longitudinal axes in the flow direction. Depending on the effluent quantity, a greater or smaller number of emitters is disposed parallel, next to one another, and one above the other, so that there is no point in the effluent flow which is more than a predetermined maximum distance from the radiation sources. In this manner, the bacteria present in the clarified effluent are reliably killed and the effluent is thus disinfected.

A UV disinfecting device of this type is known from EP 0 080 780 and corresponding U.S. Pat. No. 4,482,809. In this structure, a number of UV lamps are surrounded by cylindrical casing sleeves and, together with them, constitute lamp units. A number of lamp units are disposed horizontally, parallel to one another, and one above the other, wherein the casing sleeves are each disposed in a water-tight fashion in bases that are fixed to the frame. The inside of the casing sleeves, the inside of the bases, and the inside of the frame thus communicate with each other, so that the electric supply lines can be routed through these hollow spaces.

In this structure, it is problematical that on the one hand, this system is technically expensive. On the other hand, in order to replace a single UV lamp that has become defective, the system that is closed in a water-tight fashion has to be opened, which in particular can lead to sealing problems later, particularly when there is external contamination. Finally, there is the not-insignificant danger that with a single leak in the entire system, all of the hollow spaces that communicate with each other become flooded with effluent and, as a result, an entire vertical row of UV emitters fails and is severely damaged.

SUMMARY OF THE INVENTION

Therefore, the object of the present invention is to produce a UV disinfecting device for flowing fluids that is structurally simpler, easier to maintain, and more reliable in operation.

This object is achieved by a device with respective clamps which hold each lamp unit in place.

Because clamps are provided for securing the lamp units, individual lamp units can easily be removed from the disinfecting device without impairing the secured and water-tight assembly of the remaining lamp units. The clamps are cheap to produce, and furthermore offer the advantage that less of a flow resistance is presented, to the flow of the effluent to be disinfected, in the direction of the longitudinal axes of the individual lamp units.

A favorable service life of the securing device is achieved when the clamps are made of a corrosion-resistant spring steel, for example as punched, bent components made from a steel band.

A reliable and particularly safe configuration in electrical terms is achieved when the UV lamp is enclosed by a casing tube that is also permeable to UV radiation. A secure hold is produced, even with moderate loads on the lamp units, if the clamps have such an opening width that they grip the lamp units in their circumference region in a spring-actuated manner, with or without interposed components. The lamp units can be associated, at least in part, with retaining rings that are disposed between the casing tubes and the clamps during operation. This embodiment is particularly safe from damage to the casing tube.

In a particularly simple manner, the casing tubes can be closed in a water-tight manner, in such a way that they are closed on at least one end by a stopper made of a rubber-elastic and/or UV resistant material. This obviates the need for a complex stopper device, which has numerous sealing surfaces and therefore has numerous potential defect sources. It is particularly advantageous if, on its outer circumference, in the region that can be inserted into the casing tube, the stopper is provided with circumferential ribs that can rest in a sealed fashion against the inner surface of the casing tubes during operation. Such ribs seal in the same manner that O-rings, for example, would seal at this location. The at least one electrical connection can be routed through the stopper. The electrical connection can be secured in the stopper by being cast or vulcanized there.

In order to secure the position of the stopper of a lamp unit, it is advantageous, for example, if in each lamp unit, one or two clamps engage the respective stopper directly, and not the corresponding end of the casing tube.

It is furthermore advantageous if a wiper is provided to clean the outer surface, which wiper can slide cleaning elements that encompass the casing tubes in the axial direction of the respective casing tube, and the cleaning elements, for example in the form of stripping rings, are secured to the wiper by means of clamps, which are preferably structurally identical to the clamps for securing the lamp units. In this manner, a removal of the lamp unit from both the frame and the wiper is permitted, wherein identical components are used. If at least one stopper thereby does not protrude past the outer diameter of the casing tube, each stripping ring can be removed from the casing tube for maintenance without opening the lamp unit.

Finally, if the casing tubes each have at least one circumferential constriction or groove in whose region the lamp units are secured by the clamps, then the respective lamp unit is fixed in the axial direction and can be removed in a radial direction easily and without tools. The flow resistance is reduced further by means of this measure.

BRIEF FIGURE DESCRIPTION

DETAILED DESCRIPTION

Figure 1:
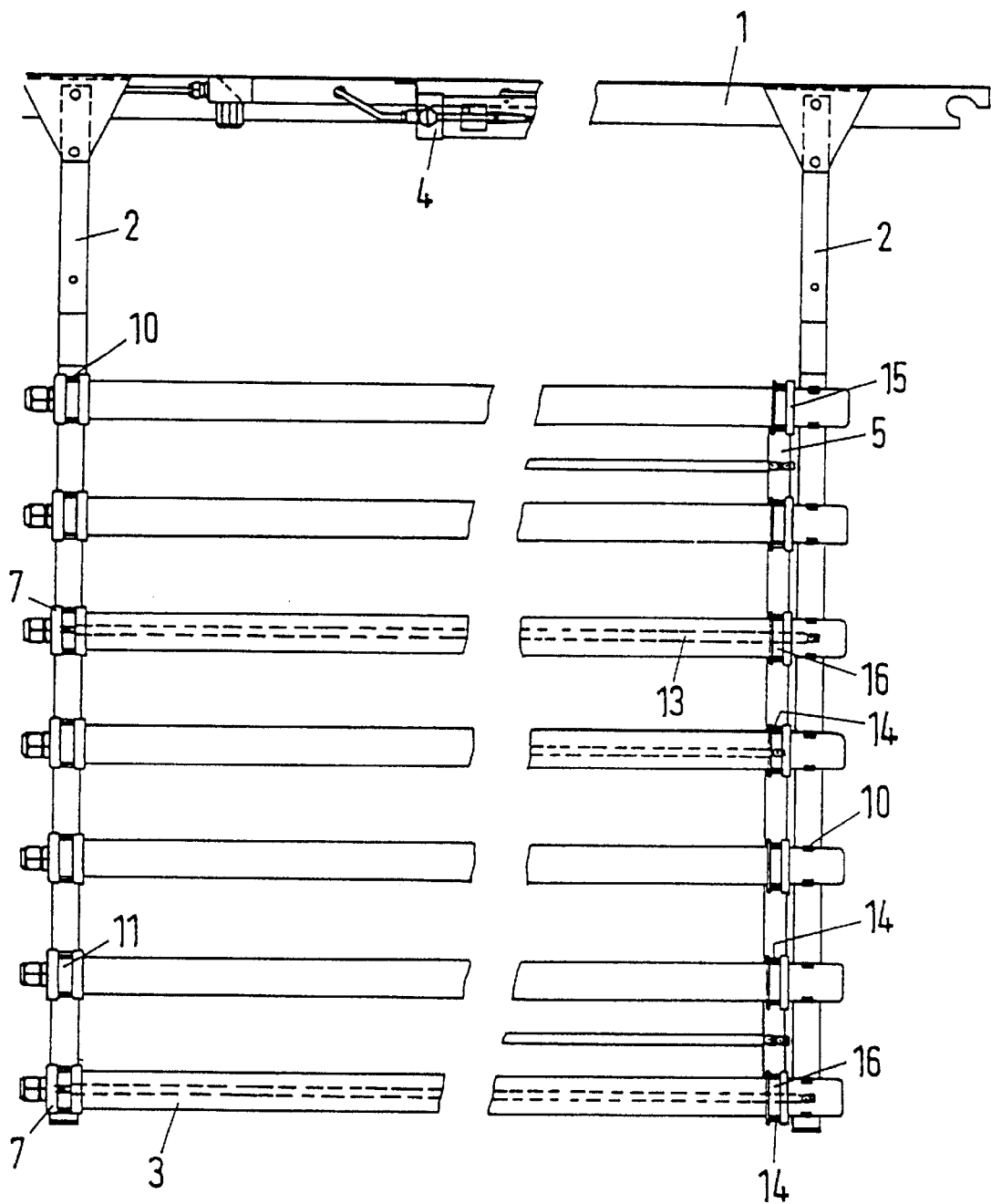
FIG. 1 shows a module of a disinfecting device according to the invention in a shortened side view.
Figure 2:
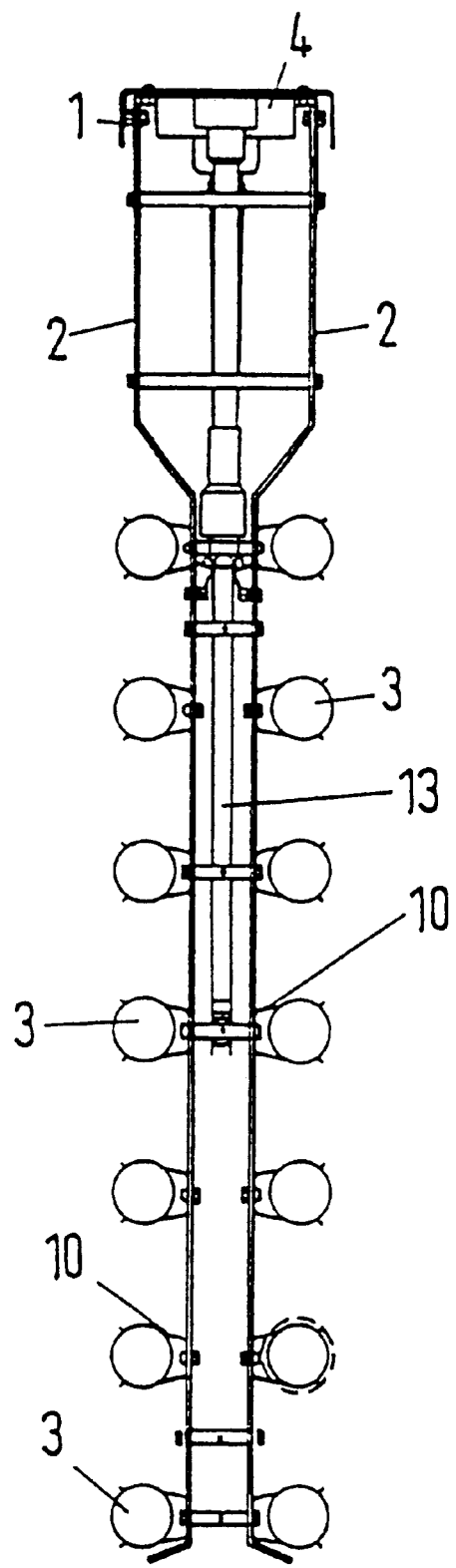
FIG. 2 shows the module according to FIG. 1 in a side view.

In FIGS. 1 and 2, a module of a UV disinfecting device is shown in a shortened side view and in an end view.

Figure 3:
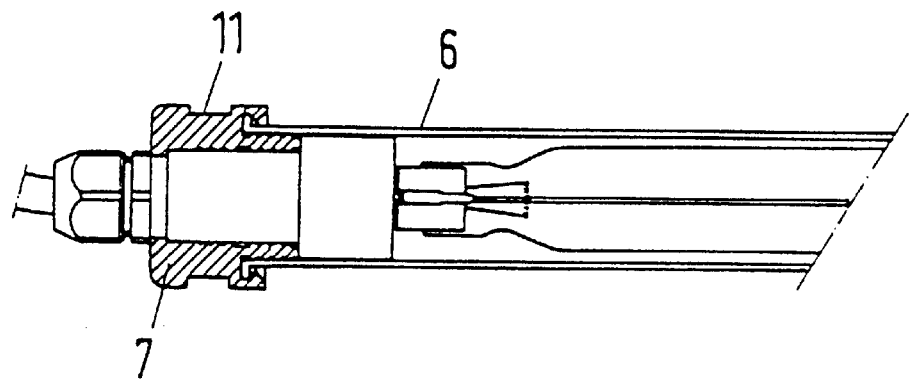
FIG. 3 shows an end of a lamp unit closed with a stopper in a cross-section from the side.

The module includes a frame support 1 that extends horizontally during operation, from which two vertical frame legs 2 extend downward in a vertical direction. The frame legs 2 in turn support a total of fourteen lamp units 3, only seven of which can be seen in FIG. 1. The horizontal frame support 1 is associated with only-partially-depicted drive means 4 for a wiper unit 5. The lamp units 3 have an essentially elongated cylindrical shape, whose outer form is defined by casing tubes 6 and a respective stopper 7, as can be seen from FIGS. 3 and 4. On their ends opposite the stopper 7, the lamp units end in one piece in a closed end.

The lamp units 3 are secured to the vertically extending frame legs 2 with clamps 10 that grip each lamp unit at both ends in a spring-actuated fashion. The respective clamp 10 grips the stopper end of the lamp unit in the vicinity of a groove 11 that runs around the stopper, while the end disposed opposite from the stopper is gripped directly in the vicinity of the surface of the casing tube 6. In this manner, the lamp unit is fixed in a definite position in the clamps because on both ends, the clamps 10 produce a spring-actuated fixing in the radial direction, while the engagement in the groove 11 in the vicinity of the stopper produces a form-fitting engagement in the axial direction. The wiper unit 5 has a pneumatic linear cylinder as a drive in the vicinity of the drive unit 4 as well as a bracing device 13 that supports a clamp 14 on the end, in the vicinity of each lamp unit. The clamps 14 are structurally identical to the clamps 10. Each clamp 14 in turn engages in a ring 15 that encompasses the corresponding casing tube 6, in which ring, the clamp 14 rests with positive fit, at least in the axial direction, in the vicinity of an annular groove 16. The ring 15 encompasses the respective casing tube 3 of a lamp unit in a snug sliding seat.

Figure 4:
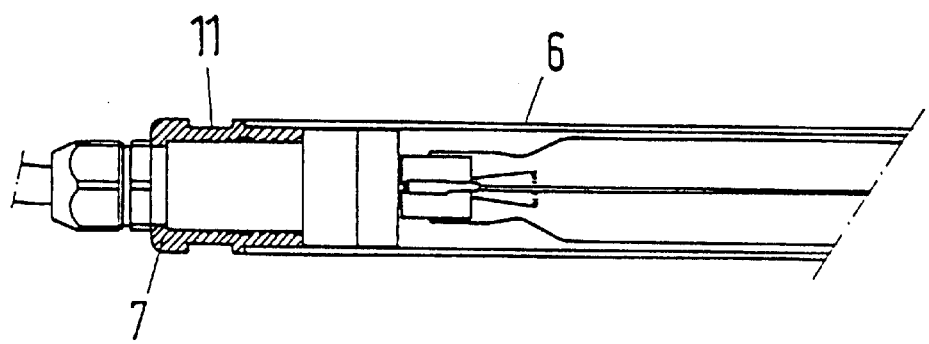
FIG. 4 shows an end of a lamp unit closed with a stopper in a cross-section from the side, wherein the stopper does not protrude beyond the casing tube in diameter.

FIG. 4 shows an end of a lamp unit closed with a stopper in a cross-section from the side, wherein the stopper 7 does not protrude beyond the casing tube 6 in diameter. This achieves the fact that the stripping ring (15) of the wiper unit 5 can also be removed by way of the connecting end of the lamp unit, without the lamp unit having to be opened. The cross-section of the lamp unit that is flowed around is thus particularly small.

Figure 5:
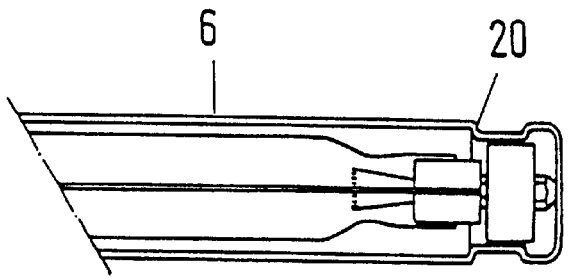
FIG. 5 shows an end of a lamp unit with a groove near the edge.

Finally, FIG. 5 shows an end of a lamp unit into which an annular groove or constriction 20 is stamped from the outside. A clamp engages in this groove in the operating position. As a result, the lamp unit is form-fittingly fixed in its longitudinal direction, while it remains easy to remove in the direction of the open end of the clamp. The engagement of the clamp in the groove 20 reduces the flow resistance. In addition, it is no longer necessary to provide a fixing in the longitudinal direction in the vicinity of the stopper 7, 11. The clamp there can engage in a smooth region of the stopper or the casing tube. A second fixing in the longitudinal or axial direction of the lamp units is generally not necessary.

During operation, the module of the UV disinfecting device is inserted into a channel, a so-called sluice, of a sewage treatment plant and emits ultraviolet radiation of a high energy density there, while the effluent to be disinfected flows around the lamp units in the horizontal direction, parallel to the axial direction of the casing tubes 6. Depending on the composition of the water, sooner or later, deposits appear on the outer surfaces of the casing tubes, which reduce the intensity of the ultraviolet radiation. Therefore, at regular intervals, the assembly 13 of the wiper unit 5 slid parallel to the axial direction of the casing tubes 6 through activation of the drive 4. In this connection, the end clamps 14 carry the rings 15 along with them and, in this manner, wipe nearly the entire surface of the casing tubes 6 clean.

If a lamp must be changed due to a defect or due to diminishing output, or if the module must have other maintenance performed on it, the operator can simply lift the corresponding module out of the sluice and manually pull the lamp unit to be serviced out of the clamps, lateral to the axial direction of the casing tubes 6. In this connection, only the securing forces of the clamps 10 and 14 have to be overcome, without the need for a tool. At the same time, the ring 15, together with the lamp unit, is detached from the wiper arrangement 5, 13, 14, and can likewise be cleaned or replaced. When there is a separate lamp unit, the stopper 7 is easy to remove from the casing tube 6. Since the stopper 7 is made of a rubber-elastic material, it can be simply pulled out of the casing tube 6, whereby the UV lamp disposed in the casing tube 6 also becomes accessible. The assembly of the lamp unit then occurs in a reverse manner, i.e. the UV lamp is inserted into the base associated with the stopper 7 which is then introduced, together with the UV lamp, into the casing tube 6.

As a result, annular ribs that are formed onto the stopper 7 rest in a sealing fashion against the inside of the casing tube 6, while the end face of the casing tube 6 is introduced into a groove of the stopper 7 and is secured there by an undercut. The sealing faces of the stopper 7 with the casing tube 6 can be easily seen from the outside through the transparent casing tube so that, in actual use, an unreliably inserted seal, for example as a result of contamination, can be detected immediately.

With the present embodiment, therefore, not only can one remove complete lamp units separately from the respective module, but the securing of the respective lamp units in clamps is also an outstandingly simple and cost-effective securing possibility which is also very reliable. This securing also presents only a slight resistance to water flowing in the axial direction so that, even with large through flow quantities, only a slight pressure loss is produced. The relatively simple sealing of the lamp units with the stoppers 7 described furthermore increases the reliability of the modules, by virtue of the fact that, even in the unlikely event of an insufficient seal, only one lamp unit would fail, rather than the entire module, with all of the lamp units, being damaged at the same time.

What is claimed is:

1. A UV disinfecting device for flowing fluids, comprising:
a frame (1);
a number of lamp units (3) having UV lamps, which units respectively have at least one electrical connection and are secured by the frame (1), said units being essentially parallel to and spaced apart from one another; and
clamps for securing the lamp units (3) to said frame (1), each of said clamps (10) having a pair of movable members to engage a lamp unit (3) in their circumference region by spring-activated engagement wherein said lamp unit (3) may be moved by the exertion of manual force on said lamp unit (3) into and out of said respective clamp (10) between said members of said clamp (10).

2. The device according to claim 1, wherein the clamps (10) are made of a corrosion-resistant spring steel.

3. The device according to claim 1, wherein the movable members of said clamps (10) are adapted to secure the lamp units (3) by engaging a respective stopper portion (7) of each lamp unit.

4. The device according to claim 1, wherein in order to clean the outer surface of the casing tubes, a wiper unit (5) is provided, which is adapted to slide cleaning elements (15), which surround respective casing tubes (6) of lamp units (3), in an axial direction of the respective casing tube (6), wherein the cleaning elements (15) are secured to the wiper unit (5) by means of clamps (14) that are structurally identical to the clamps (10) for securing the lamp units (3).

5. The device according to claim 1, wherein the casing tubes each having at least one circumferential constriction of groove (11, 20) for engagement with said members of said clamps (10).

6. The device according to claim 5, wherein the lamp units (3) are secured by said clamps (10) in the region of the groove (11, 20), wherein the clamps are adapted to grip the lamp units directly and fix them in a predetermined axial direction.

7. The device according to claim 1, wherein each casing tube (6) is closed on at least one end by a stopper (7) made of UV-resistant material.

8. The device according to claim 1, wherein each casing tube (6) is closed on at least one end by a stopper (7) made of elastomeric, UV-resistant, material.

9. The device according to claim 1, wherein each UV lamp is surrounded by a respective casing tube (6).

10. The device according to claim 9, wherein the lamp units (3) are at least partially associated with rings (15) that are disposed between the casing tubes (6) and the clamps (10) during operation and serve as rings for stripping any deposited material from outer surfaces of the casing tubes (6).

11. The device according to claim 9, wherein the casing tubes (6) are closed on at least one end with a stopper (7) made of elastomeric material.

12. The device according to claim 11, wherein on its outer circumference, in a region adapted for insertion into the casing tube (6), the stopper (7) is provided with circumferential ribs that rest in a sealing fashion against an inner surface of the casing tube (6) during operation.

13. The device according to claim 11, wherein the stopper (7) has a circumferential groove (11) that is open in the axial direction, into which an end face of the casing tube (6) can be inserted.

14. The device according to claim 11, wherein the at least one electrical connection is routed through the stopper (7).

15. The device according to claim 9, wherein the lamp units (3) are at least partially associated with rings (15) that are disposed between the casing tubes (6) and the clamps (10) during operation, the rings serving as retaining rings for devices for stripping any deposited material from outer surfaces of the casing tubes (6).

16. The device according to claim 9, wherein a clamp (10) is located proximate each end of a lamp unit (3).

17. The device according to claim 16 wherein each casing tube (6) is closed at each end by a stopper (7) having an annular groove (11) and the members of each clamp (10) proximate said end, engage said annular groove (11) to fix the lamp unit (3) in a definite position in the clamps (10) both radially and axially relative to said frame (1).

18. The device according to claim 17 wherein said members of each of said clamps (10) securing a given lamp unit (3) are aligned to allow movement in a given direction of said lamp unit (3) into and out of engagement with said respective clamps (10).

19. The device according to claim 18 further comprising:
   a wiper unit (5) having a cleaning ring (15) encircling a casing tube (6) of each of said lamp units (3);
   means to move said wiper unit (5) and each of said rings (15) axially along said casing tubes (6) to clean the circumference of each of said casing tubes (6); and
   clamps (14) that are structurally identical to clamps (10) to secure said cleaning rings (15) to said wiper unit (5).

* * * * *